United States Patent
Jin

(10) Patent No.: US 7,157,278 B2
(45) Date of Patent: Jan. 2, 2007

(54) CULTURED CELLS FROM PANCREATIC ISLETS

(75) Inventor: Jianjian Jin, Quincy, MA (US)

(73) Assignee: Organogenesis, Inc., Canton, MA (US)

( * ) Notice: Subject to any disclaimer, the term of this patent is extended or adjusted under 35 U.S.C. 154(b) by 0 days.

(21) Appl. No.: 10/497,508

(22) PCT Filed: Dec. 4, 2002

(86) PCT No.: PCT/US02/38848

§ 371 (c)(1),
(2), (4) Date: Oct. 28, 2004

(87) PCT Pub. No.: WO03/048336

PCT Pub. Date: Jun. 12, 2003

(65) Prior Publication Data

US 2005/0048032 A1 Mar. 3, 2005

Related U.S. Application Data

(60) Provisional application No. 60/337,205, filed on Dec. 4, 2001.

(51) Int. Cl.
*C12N 5/08* (2006.01)
*C12N 5/00* (2006.01)

(52) U.S. Cl. .................................... 435/366; 435/325

(58) Field of Classification Search ............... 435/366, 435/325
See application file for complete search history.

(56) References Cited

OTHER PUBLICATIONS

Levin F, No pancreatic endocrine stem cells?, 2004, NEJM, vol. 351, pp. 1024-1026.*
Beattie GM, Sustained proliferation of PDX-1 cells derived from human islets, 1999, Diabetes, vol. 48, pp. 1013-1019.*
Esni F, Orgin of exocrine pancreatic cells from nestin-positive precursors in developing mouse pancreas, 2004, Mech. of Develop. vol. 121, pp. 15-25.*
rothr KI, Challenges facing islet transplantation for the treatment of type 1 diabetes-mellitus, 2004, JCI, vol. 114, pp. 877-883.*

* cited by examiner

*Primary Examiner*—Dave Trong Nguyen
*Assistant Examiner*—David A. Montanari
(74) *Attorney, Agent, or Firm*—Kramer Levin Naftalis & Frankel

(57) ABSTRACT

A cell composition of endocrine progenitor cells derived from mammalian pancreatic islet cells that can be transplanted into a diabetic patient such that the cells of the cell composition differentiates into functioning insulin-producing beta cells.

2 Claims, 2 Drawing Sheets

CULTURED CELLS FROM PANCREATIC ISLETS

FIELD OF THE INVENTION

The present invention pertains to the field of diabetes and pancreatic islets and more particularly relates to endocrine progenitor/precursor cells from pancreatic islet cells that have the potential to be differentiated into functioning insulin-producing beta-cells.

BACKGROUND OF THE INVENTION

Diabetes mellitus is a significant health problem, affecting approximately 16 million people in the United States. Loss of sufficient insulin production by the pancreatic islet beta cell is a hallmark of both type I and type II diabetes. Replacement of these cells through regeneration or transplantation could offer lifelong treatment for diabetics. However, a major problem in implementing treatment is the lack of sufficient islet cell tissue for transplantation. It has been reported that in the U.S. only about 3,000 human donor pancreases are available each year, yet over 35,000 new cases of type I diabetes are diagnosed each year. There is a continuing need for a method of treating a diabetic patient by transplantation of cells that will function as insulin-producing pancreatic islet cells.

SUMMARY OF THE INVENTION

The invention is a cell composition comprising endocrine progenitor/precursor cells from a mammalian pancreas, preferably a human pancreas, and typically an adult pancreas, that have been cultured in serial passages in a defined culture medium and that express islet progenitor markers pdx1 and nestin. The endocrine progenitor/precursor cells are cultured in a defined culture medium over multiple passages to expand cell numbers. As the cells expand, they become more proliferative and less differentiated. When a sufficient number of cells are obtained, the cell composition of the invention comprising the endocrine progenitor/precursor cells may be used to make living cell implants to treat one or more patients with insulin deficient diabetes.

DETAILED DESCRIPTION

Figure 1:
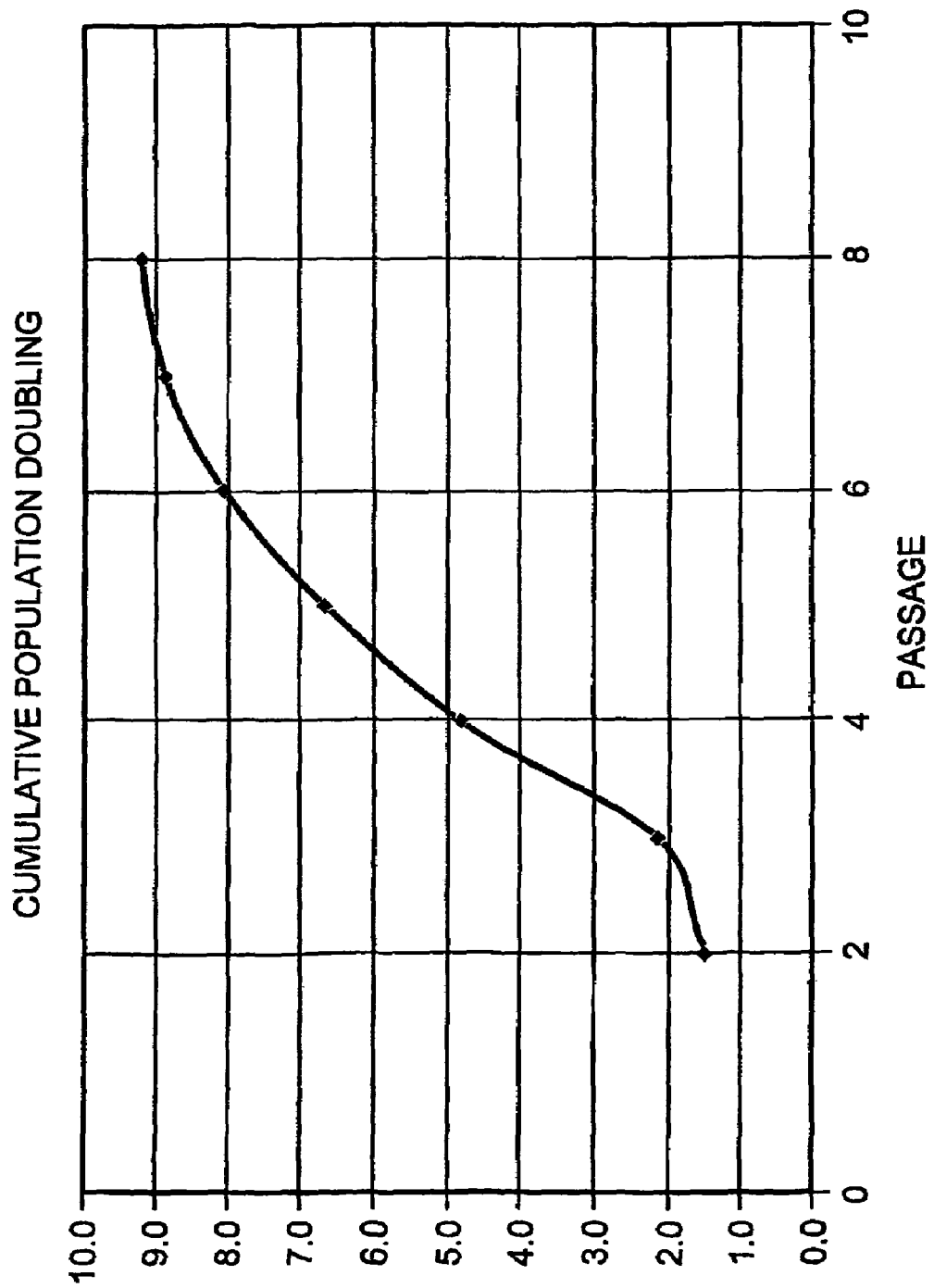
FIG. 1 shows the table and graph of cumulative population doubling of human islet-derived cells H297.

One feature of the invention is a cell composition of endocrine progenitor/precursor cells from mammalian pancreatic islets, typically adult pancreas islet cells, characterized by less differentiation than the initial derived cells prior to culturing in serial passages in defined medium.

Another feature of the invention is a defined culture medium formulation for the culture of endocrine precursor cells.

A further feature of the invention is a method for culturing cells from mammalian pancreatic islets in serial passages resulting in endocrine progenitor/precursor cells that are less differentiated than the initial cells of the culture.

The cells used to initiate the cell composition of the invention are derived from mammalian pancreatic islets, preferably human pancreatic islets, and typically adult pancreas islet cells. Following the described culturing methods of the invention, these initial pancreatic islet cells are cultured in defined culture medium and expanded through serial passages in defined culture medium, resulting in less differentiated endocrine progenitor/precursor cells that express islet progenitor markers pdx-1 and nestin. The endocrine progenitor/precursor cells have the potential to be differentiated into functioning insulin-producing beta-cells. As used herein, "endocrine progenitor/precursor cells," "endocrine progenitor cells," and "endocrine precursor cells" are all intended to refer to cells derived from mammalian pancreatic islets that are capable of serial passages in defined culture medium, are less differentiated than the initial cells prior to culturing, and that express markers pdx1 and nestin. In the cell composition of the invention, the endocrine progenitor cells differentiate into functioning insulin-producing beta cells when implanted into a patient to treat insulin deficient diabetes.

The medium used to culture the initial pancreatic cells and serial passage into endocrine precursor cells is chemically defined, meaning that it contains no serum or. organ extracts. The medium is able to culture and maintain endocrine precursor cells over several passages to expand the cell numbers of the population. The ability to expand the cell numbers is beneficial where human pancreatic tissue is limited. An additional benefit is that a number of therapeutic cell compositions can be produced from a single pancreas.

The defined culture medium is comprised of a nutrient base usually further supplemented with other components. The skilled artisan can determine appropriate nutrient bases in the art of animal cell culture with reasonable expectations for successfully producing a tissue construct of the invention. Many commercially available nutrient sources are useful on the practice of the present invention. These include commercially available nutrient sources which supply inorganic salts, an energy source, amino acids, and B-vitamins such as Dulbecco's Modified Eagle's Medium (DMEM); Minimal Essential Medium (MEM); M199; RPMI 1640; Iscove's Modified Dulbecco's Medium (EDMEM). Minimal Essential Medium (MEM) and M199 require additional supplementation with phospholipid precursors and nonessential amino acids. Commercially available vitamin-rich mixtures that supply additional amino acids, nucleic acids, enzyme cofactors, phospholipid precursors, and inorganic salts include Ham's F-12, Ham's F-10, NCTC 109, and NCTC 135. Albeit in varying concentrations, all basal media provide a basic nutrient source for cells in the form of glucose, amino acids, vitamins, and inorganic ions, together with other basic media components.

The preferred base medium of the invention comprises a nutrient base of either calcium-free or low calcium Dulbecco's Modified Eagle's Medium (DMEM), without glucose, magnesium, and with L-glutamine at 4.0 mM, without sodium pyruvate, and with Ham's F-12 (with 5 mM glucose) in a 3-to-1 ratio. The final glucose concentration of the base is adjusted to between about 2 mM to about 8 mM, more preferably between about 3 mM to about 7 mM, and most preferably at about 5 mM.

The base medium is supplemented with components such as amino acids, growth factors, and hormones. Defined culture media for the culture of cells of the invention are described in U.S. Pat. No. 5,712,163 to Parenteau and in International PCT Publication No. WO 95/31473, the disclosures of which are incorporated herein by reference. Other media are known in the art such as those disclosed in Ham and McKeehan, Methods in Enzymology, 58:44–93

(1979), or for other appropriate chemically defined media, in Bottenstein et al., Methods in Enzymology, 58:94–109 (1979).

In the preferred embodiment, the base medium is supplemented with the following components known to the skilled artisan in animal cell culture: insulin, transferrin, triiodothyronine (T3), either or both ethanolamine and o-phosphoryl-ethanolamine, epidermal growth factor, hydrocortisone, selenium, adenine, strontium chloride, sodium pyruvate, non-essential amino acids, soybean trypsin inhibitor (SBTI), and glucose. Concentrations and substitutions for the supplements may be determined by the skilled artisan by carrying out titration experiments.

Insulin is a polypeptide hormone that promotes the uptake of glucose and amino acids to provide long term benefits over multiple passages. Supplementation of insulin or insulin-like growth factor (IGF) is necessary for long term culture as there will be eventual depletion of the cells' ability to uptake glucose and amino acids as well as possible degradation of the cell phenotype. Insulin supplementation is advisable for serial cultivation and is provided to the media at a concentration range of preferably between about 0.5 µg/ml to about 50 µg/ml, more preferably between about 5 µg/ml to about 15 µg/ml, and most preferably at about 10 µg/ml. Appropriate concentrations for the supplementation of insulin-like growth factor, such as IGF-1 or IGF-2, used in place of insulin may be easily determined by one of skill in the art by carrying out a simple titration experiment for the cell types chosen for culture.

Transferrin is in the medium for iron transport regulation. Iron is an essential trace element found in serum. As iron can be toxic to cells in its free form, in serum it is supplied to cells bound to transferrin at a concentration range of preferably between about 0.05 µg/ml to about 50 µg/ml, more preferably between about 5 µg/ml to about 15 µg/ml, and most preferably at about 5 µg/ml.

Triiodothyronine (T3) is a basic component and is the active form of thyroid hormone that is included in the medium to maintain rates of cell metabolism Triiodothyronine is supplemented to the medium at a concentration range between about 0 to about 400 pM, more preferably between about 2 pM to about 200 pM, and most preferably at about 20 pM.

Either or both ethanolamine and o-phosphoryl-ethanolamine, which are phospholipids, are added whose function is an important precursor in the inositol pathway and fatty acid metabolism. Supplementation of lipids that are normally found in serum is necessary in a serum-free medium. Ethanolamine or o-phosphoryl-ethanolamine, or both, are provided to media at a concentration range between about $10^{-6}$ M to about $10^{-2}$ M, more preferably at about $1\times10^{-4}$ M.

Hydrocortisone has been shown to have benefits when culturing other epithelial cell types, to promote phenotype and therefore enhance differentiated characteristics (Rubin et al., J. Cell Physiol., 138:208–214 (1986)). Hydrocortisone may be provided at a concentration range of about 0.04 µg/ml to about 4.0 µg/ml, preferably at about 0.4 µg/ml.

Selenium is added to serum-free media to resupplement the trace elements of selenium normally provided by serum. Selenium may be provided at a concentration range of about $10^{-9}$ M to about $10^{-7}$ M; most preferably at about $5.3\times10^{-8}$ M.

The amino acid L-glutamine is present in some nutrient bases and may be added in cases where there is none or insufficient amounts present. L-glutamine may also be provided in stable form such as that sold under the mark, GlutaMAX-1™ (Gibco BRL, Grand Island, N.Y.). GlutaMAX-1™ is the stable dipeptide form of L-alanyl-L-glutamine and may be used interchangeably with L-glutamine and is provided in equimolar concentrations as a substitute to L-glutamine. The dipeptide provides stability to L-glutamine to protect it from degradation over time in storage and during incubation that can lead to uncertainty in the effective concentration of L-glutamine in medium. Typically, the base medium is supplemented with glutamine at a concentration preferably between about 1 mM to about 10 mM, more preferably between about 2 mM to about 8 mM, and most preferably 6 mM L-glutamine.

Growth factors such as epidermal growth factor (EGF) may also be added to the medium to aid in the establishment of the cultures through cell scale-up and seeding. EGF in native form or recombinant form may be used Human forms, native or recombinant, of EGF are preferred for use in the medium when fabricating a skin equivalent containing no non-human biological components. EGF is an optional component and may be provided at a concentration between about 1 to 15 ng/mL, more preferably between about 5 to 10 ng/mL.

The defined medium described above is typically prepared as set forth below. However, it should be understood that the components of the defined medium may be prepared and assembled using any conventional methodology compatible with their physical properties. It is well known in the art to substitute certain components with an appropriate analogue or functionally equivalent acting agent for the purposes of availability or economy and arrive at a similar result Naturally occurring growth factors may be substituted with recombinant or synthetic growth factors that have similar qualities and results when used in culturing. The optimal concentration for the supplements may have to be adjusted slightly for cells derived from different mammalian species and cell lines from different donors will vary in their performance due to its age, size, and health. Titration experiments are performed with varying concentrations of a component to arrive at the optimal concentration for that component.

Media in accordance with the present invention are sterile. Sterile components are bought or rendered sterile by conventional procedures, such as filtration, after preparation. Proper aseptic procedures were used throughout the following Examples. DMEM and F-12 are combined and the individual components are then added to complete the medium. Stock solutions of all components can be stored at −20° C., with the exception of nutrient source that can be stored at 4° C. All stock solutions are prepared at 500× final concentrations listed above. A stock solution of insulin, transferrin and triiodothyronine (all from Sigma) is prepared as follows: triiodothyronine is initially dissolved in absolute ethanol in 1N hydrochloric acid (HCl) at a 2:1 ratio. Insulin is dissolved in dilute HCl (approximately 0.1N) and transferrin is dissolved in water. The three are then mixed and diluted in water to a 500× concentration. Ethanolamine and o-phosphoryl-ethanolamine are dissolved in water to 500× concentration and are filter sterilized. Hydrocortisone is dissolved in absolute ethanol and diluted in phosphate buffered saline (PBS). Selenium is dissolved in water to 500× concentration and filter sterilized. EGF is purchased sterile and is dissolved in PBS. Adenine is difficult to dissolve but may be dissolved by any number of methods known to those skilled in the art. Human serum albumin (HSA) or bovine serum albumin (BSA) may be added for prolonged storage to maintain the activity of the EGF stock solutions. The medium can be either used immediately after preparation or, stored at 4° C. If stored, EGF should not be added until the time of use.

A more preferred culture medium formulation for serial culture of the endocrine precursor cells of the invention comprises: a base 3:1 mixture of Dulbecco's Modified Eagle's Medium (DMEM) (no glucose, no calcium, with 4 mM L-glutamine) and Hams F-12 medium, and the base is supplemented with the following components with the final concentration of each component indicated. 6 mM L-glutamine (or equivalent), 10 ng/ml epidermal growth factor, 0.4 µg/ml hydrocortisone, $1\times10^{-4}$ M ethanolamine, $1\times10^{-4}$ M o-phosphorylthanolainine, 5 µg/ml insulin, 5 µg/mL transferrin, 20 pM trijodothyronine, 6.78 ng/ml selenium, 24.4 µg/mL adenine, 266.6 µg/mL strontium chloride, 100 mM sodium pyruvate, 10 mM non-essential amino acids, 12.5 mg/mL soybean trypsin inhibitor (SBTI), and 5 mM glucose The endocrine precursor cells are cultured in a vessel suitable for animal cell or tissue culture, such as a culture dish, flask, or roller-bottle, which allows for the formation of a three-dimensional tissue-like structure. Suitable cell growth surfaces on which the cells can be grown can be any biologically compatible material to which the cells can adhere and-provide an anchoring means for the cell-matrix construct to form. Materials such as glass, stainless steel, polymers, including polycarbonate, polystyrene, polyvinyl chloride, polyvinylidene, polydimethylsiloxane, fluoropolymers, and fluorinated ethylene propylene; and silicon substrates, including fused silica, polysilicon, or silicon crystals may be used as a cell growth surfaces. The cell growth surface material may be chemically treated or modified, electrostatically charged, or coated with biologicals such as with peptides. An example of a peptide coating is RGD peptide.

While the cells of the invention may be grown on a solid cell growth surface or a cell growth surface with pores, such as a porous membrane, that communicate both top and bottom surfaces of the membrane to allow bilateral contact of the medium to the culture. Bilateral contact allows medium to contact both the top and bottom surfaces of the culture for maximal surface area exposure to the nutrients contained in the medium. The pores in the growth surface allow for the passage of culture media for providing nutrients to the underside of the culture through the membrane, thus allowing the cells to be fed bilaterally. Culture vessels incorporating a porous membrane are known in the art and are preferred for carrying out the invention and are described in a number United States patents in the field, some of which have been made commercially available, including for instance: U.S. Pat. Nos. 5,766,937, 5,466,602, 5,366,893, 5,358,871, 5,215,920, 5,026,649, 4,871,674, 4,608,342, the disclosures of which are incorporated herein by reference. A preferred pore size is one that is small enough that it does not allow for the growth of cells through the membrane, yet large enough to allow for free passage of nutrients contained in culture medium to the bottom surface of the cell culture, such as by capillary action. Preferred pore sizes are about less than 3 microns but range between about 0.1 microns to about 3 microns, more preferably between about 0.2 microns to about 1 micron and most preferably about 0.4 micron to about 0.6 micron sized pores are employed.

The cultures are maintained in an incubator to ensure sufficient environmental conditions of controlled temperature, humidity, and gas mixture for the culture of cells. Preferred conditions are between about 34° C. to about 38° C., more preferably 37±1° C. with an atmosphere between about 5–10±1% $CO_2$ and a relative humidity (Rh) between about 80–90%.

The defined culture medium allows for establishing primary cultures and serial passaging of the cultures, thus providing for an expanded number of cells for using the cells for testing or as a therapeutic. One of the hurdles in human islet cell culture is fibroblast overgrowth that could overshadow the growth of the targeted epithelial cells, a subpopulation with characteristics of islet progenitor/precursor cells. Culturing the cells with the defined medium has overcome this problem The cells grown from human islets using this defined medium have shown predominantly epitheloid-like morphology and expressed the cytokeratin epithelial marker.

At each passage of the cells, the markers specific to both progenitor cells and endocrine precursor cells continue to be exhibited by the cells, including pdx1 and nestin. The cultured cells exhibit a decrease in the expression of islet cell markers indicating the cells may dedifferentiate with each passage; however, the cells maintain progenitor phenotype throughout each passage.

Pdx1, a transcription factor also known as IDX-1, is a known marker of pancreatic differentiation and regulator of pancreatic development. (Jonsson et al. Nature 371:606 (1994) and Offield et al. Development 122:983 (1996)).

Nestin is a cellular marker for developing pancreatic islet cells. (Lendahl, et al. Cell 60:585–595 (1990) and Zulewski et al. Diabetes. 2001 March;50(3):521–33.)

The endocrine precursor cells may be induced to differentiate using chemical or physical means, such as by supplementing the culture medium with an agent that promotes differentiation to insulin-producing beta cells or by way of forming cell clusters in a matrix, such as an extracellular matrix. Inplant-induced differentiation (in vivo) of the cells in the right environment will induce the cells to differentiate. The cells may be implanted subcutaneously, in the submucosa of the small intestine, or under the kidney capsule.

The following examples are provided to better explain the practice of the present invention and should not be interpreted in any way to limit the scope of the present invention. Those skilled in the art will recognize that various modifications can be made to the methods described herein while not departing from the spirit and scope of the present invention.

EXAMPLES

Example 1

Isolation of Pancreatic Small Cells from Cadaveric Human Pancreata

Human pancreatic islet isolation was performed by the semi-automated method originally proposed by Ricordi (Ricordi C, Lacy P E, Finke E H, et al. Automated method for isolation of human pancreatic islets. Diabetes 1988 37:413–420). Procured pancreases were distended by intraductal infusion of a Liberase HI (Roche Molecular Biochemicals, Indianapolis, Ind.) or Serva Collagenase (Cresent Chemical, Brooklyn, N.Y.) (linetsky E, Bottno R, Ehmann R, et al. Improved human islet isolation using a new enzyme blend, Liberase. Diabetes 1997 46:1120–1123), and then dissociated using the automated method (Ricordi C, Lacy P E, Finke E H, et. Al. Automated method for isolation of human pancreatic islets. Diabetes 1988 37:413–420). The separation occurs during a process of continuous digestion lasting approximately 12–30 minutes, after which the digestion circuit was cooled and the tissue collected into approximately 8 liters of cold Hanks solution and washed. Liberated islets were separated from non-islet tissue on a continuous gradient of Euroficoll in a Cobe 2991 cell separator.

Preparations of partially purified islets from the Cobe cell separator were then passed through a series of different size steel mesh screens (100 to 25μpores), and the tissue that is retrieved was placed into culture directly on plastic in culture medium and permitted to spread out.

Example 2

Isolation of Porcine Islet Cells

Pancreatic islet cells were isolated from a porcine donor and plated using the defined medium to obtain a culture with an epithelial-like phenotyye. The isolation of porcine islet cells procedure is as follows. Two Nalgene containers, several 50 mL round bottom centrifuge tubes, trays, and screens were autoclaved. Two solutions were prepared, UW-D organ preservation solution and three concentrations, 27%, 24.6%, and 11%, of FICOLL solution.

The UW-D organ preservation solution was made according to the specifications given by Sumimoto et al (Transplantation July 1989; 48(1): 1–5). One liter of 1× UW-D organ preservation solution consisted of 35.83 g of lactobionic acid (Aldrich, Milwaukee, Wis.), 17.83 g raffinose (Sigma, St. Louis, Mo.), 1.23 g $MgSO_4$ (Sigma, St. Louis, Mo.), 0.92 g glutathione (Sigma, St. Louis, Mo.), 0.136 g allopurinol (Sigma, St. Louis, Mo.), and 3.40 g monobasic potassium phosphate (Sigma, St. Louis, Mo.) and double-distilled water. This solution was then filter-sterilized using a 0.2 u filter and stored at 4° C. until needed.

The FICOLL solutions were prepared from a Eurocollins base. Eurocollins base solution (pH 7.3) consisted of 4.1 g monobasic potassium phosphate (Sigma, St. Louis, Mo.), 14.8 g dibasic potassium phosphate (Sigma, St. Louis, Mo.), 2.24 g potassium chloride (Sigma, St. Louis, Mo.), 1.68 g sodium bicarbonate (Sigma, St. Louis, Mo.), 70 g-D-Glucose (Sigma, St. Louis, Mo.) and an adequate amount of double-distilled water to bring it up to 2 liters. One liter of Eurocoliins base solution was added to 500 g of FICOLL (Sigma, St. Louis, Mo.). The FICOLL was allowed to go into solution, a process that took about 2 hours. Another 500 mL of Eurocollins was added. The solution was analyzed for BRIX and Refractive index ranges, 28–28.4 and 1.3774–1.3779$n_0$ respectively. Additional Eurocollins base was added as needed. The FICOLL solution was then filtered sterilized using a MILLIPORE-MLLIPACK (Millipore, Bedford, Mass.) and distributed into sterile 1L bottles. To prepare the 24.6% FICOLL solution, 456 mL of the stock (27%) FICOLL was diluted with 44 mL Eurocollins solution. To create the 11% FICOLL solution, 204 mL stock FICOLL was diluted with 296 mL Eurocollins. The FICOLL solutions were stored at 5° C. until needed.

The pancreas was obtained from a mixed breed pig weighing more than 40 pounds (≅20 kg). The pig had been fed a normal diet and was fasted for 24 hours prior to surgery. A cooler filled with ice, 500 mL of cold UW solution, 10 and 30 c.c. syringes, and 20-gauge angiocatheters were used in the harvest and transport of the pancreas. Once the pancreas was removed, it was perfused with cold UW solution until swollen. It was then placed in a 250 mL Nalgene container and put on ice.

During collection of the pancreas, a water bath was heated to 41° C. and a filter-sterilized Liberase PI solution (Roche Molecular Biochemicals, Indianapolis, Ind.) prepared. In order to facilitate the liberase infusion of the pancreas, dissection trays, large and small forceps, extra angiocaths, 30 and 60 c.c. syringes, and Nalgene containers were placed in the sterile field of the biological safety cabinet The organ was then removed from the ice and put onto the dissection tray. Liberase PI solution was perfused into the organ. This step was done slowly to avoid disturbing the cannulae placed there during surgery and also to prevent backflow. Once the organ was full, it was placed into another Nalgene container with some additional Liberase solution. The container was sealed and placed in the 41° C. water bath to incubate.

The pancreas was then digested until it appeared to begin separating, a process that took between 15–30 minutes. Before returning the organ to the sterile biological safety cabinet, the Nalgene container was sprayed with ethyl alcohol to insure sterility. The organ was then placed on the separating screen and gently scraped with cell scrapers for 5–10 minutes. Wash media was frequently added to facilitate the dissociation of the tissue. The wash media consisted of modified Hank's balanced salt solution (HBSS) (with calcium and magnesium, no phenol red) (JRH Biosciences, Lenexa, Kans.), donor herd horse serum (JRH Biosciences, Lenexa, Kans.), streptomycin 10,000 ug/mL (Invitrogen Life Technologies, Carlsbad, Calif.), gentamycin sulfate 50 mg/mL (OI P/N 100–50), fungizone 250 mg/mL (Invitrogen Life Technologies Carlsbad, Calif.), Amphotericin B (Invitrogen Life Technologies, Carlsbad, Calif.), and sodium desoxycholate 205 mg/mL (Invitrogen Life Technologies, Carlsbad, Calif.).

The underside of the screen was scraped to ensure that no islet cells were left behind. The wash/cell solution was then placed in large centrifuge bottles and then spun down at 700 rpms for a minute and a half. The supernatant was then carefully aspirated off. The content of each bottle was resuspended using wash media that was consolidated into one centrifuge bottle. Wash media was added until the bottle was full and then centrifuged again. The supernatant was then aspirated off and the volume of tissue determined.

To begin the density separation, 5 mL of 24.6% FICOLL was added for each mL tissue. The suspension was then mixed well and added to a 50 mL round bottom tube. In each tube, there should be no more than 12 mL of this suspension. A second layer of 27% FICOLL was added to the top of the suspension. A third layer of 11% FICOLL was added to the top of the gradient. Special care was taken to ensure that the layers did not mix. The tubes were then loaded into a centrifuge and spun down at 1700 rpms for 18 minutes. In order to maintain the gradient, the acceleration of the centrifuge was slowed and the brake disengaged.

To collect the islet cells, the 11–24.6% interface layer was removed. The islet cells and wash media were added to a wash tube and spun down for 5 minutes at 1000 rpm. The supernatant was removed and the islet cells resuspended with more wash media. This resuspension and centrifugation was repeated three times. The islet cells were then resuspended with culture media and plated.

Example 3

Islet Cell Culture

The islets cells acquired by the method of Example 1 were then plated to 60 mm tissue-culture treated culture dishes. The medium used in this example included the following: a base 3:1 mixture of Dulbecco's Modified Eagle's Medium (DMEM) (no glucose, no calcium, with 4 mM L-glutamine) and Hams F-12 medium, and the base is supplemented with the following components with the final concentration of each component indicated: 2 mM L-glutamine (or equivalent), 10 ng/ml epidermal growth factor, 0.4 µg/ml hydrocortisone, $1\times10^{-4}$ M ethanolamine, $1\times10^{-4}$ M o-phosphorylethanolamine, 5 µg/ml insulin, 5 µg/ml transferrin, 20 pM triiodothyronine, 6.78 ng/ml selenium, 24.4 µg/mL adenine, 266.6 µg/mL strontium chloride, 100 mM sodium pyruvate, 10 mM non-essential amino acids, 12.5 mg/mL soybean trypsin inhibitor (SBTI), and 5 mM glucose.

Human islet cells were cultured from primary cultures derived from the pancreatic tissue as described in Example 1 and passaged to passage 8 in the defined culture medium (identified as "H297" in the Figures). FIG. 1 shows the cumulative population doublings for each passage.

Human islet cells were plated to the culture dishes (previously coated with 0.05 mg/mL collagen for 30 minutes) and spread out from the islet clusters as early as day 1 after the plating, and grew slowly during the first week. Around day 10, small, mitotically active cells started to emerge and form colonies. These colonies expanded quickly and eventually merged together to form a population with epithelial morphology within 3–4 days. After splitting the cell culture and passing them to new culture dishes, the sub-cultured cells proliferated very fast with doubling time around 30 hours. These cells maintained proliferative capability for at least 7 passages, and the total population doubling reached up to 9.

Example 4

Characterization Studies

Figure 2:
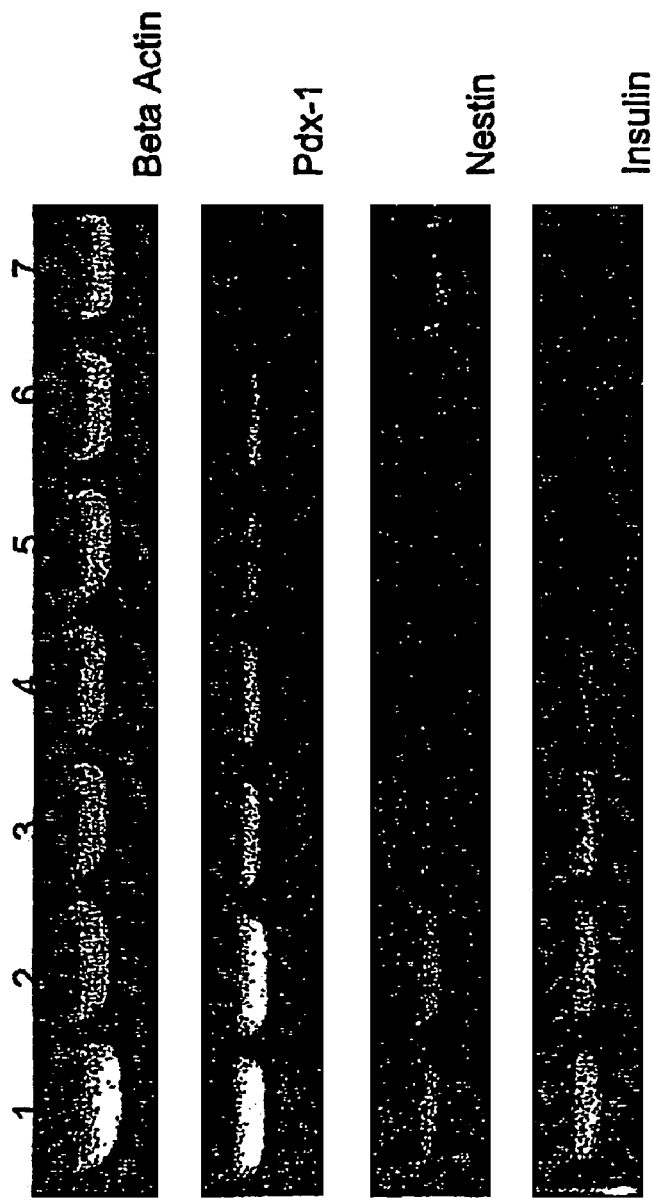
FIG. 2 shows RT-PCR analysis of pdx1, nestin and insulin expression in human islet-derived cells H297.

To characterize the expanded cell population, the expression of islet stem/progenitor markers pdx1 and nestin as well as islet hormone insulin was examined by RT-PCR, as shown in FIG. 2. H297 cells from passages 0, 2, 4, and 8 were all positive for pdx1 expression. The level of pdx1 expression seems to be relatively constant throughout the culture period. Similar expression pattern of nestin has also been detected in the cells from all these passages. The continued expression of both pdx1 and nestin in the expanded cells suggests the possibility of existence of islet stem/progenitor cells in the culture, and indicates the potential of the expansion strategy for cell based therapy. The expression of insulin, as expected, can only be detected from the cells from early passages. At passage 4, virtally no insulin mRNA signal can be detected. This result is consistent with the immunfluorescence result in which few insulin-positive cells were observed in cells from passage 4 (data not shown). The decrease of insulin signal suggests that the expanding cells are more proliferative and less differentiated.

The invention claimed is:

1. An isolated cell composition comprising human endocrine precursor cells in defined medium absent fibroblast overgrowth, and wherein said cells express markers pdx1 and nestin, and when said cells are differentiated further produce insulin.

2. A method of culturing human mammalian pancreatic islet cells to produce endocrine precursor cells comprising the steps of:
 (a) isolating human mammalian pancreatic islet cells from a pancreas of a donor;
 (b) serially culturing the cells of step (a) in a defined culture medium to expand the cells, wherein the defined culture medium comprises amino acids, growth factors, hormones, and lipids in the absence of serum or organ extracts, and
 (c) continuing to culture the cells to produce endocrine precursor cells in absence of fibroblast overgrowth, wherein the endocrine precursor cells express markers pdx1 and nestin, and further produce insulin.

* * * * *